(12) United States Patent
Nallakrishnan

(10) Patent No.: US 8,585,735 B2
(45) Date of Patent: Nov. 19, 2013

(54) HANDLE FOR SURGICAL FORCEPS AND THE LIKE

(76) Inventor: Ravi Nallakrishnan, Westmont, IL (US)

( * ) Notice: Subject to any disclaimer, the term of this patent is extended or adjusted under 35 U.S.C. 154(b) by 0 days.

(21) Appl. No.: 13/105,508

(22) Filed: May 11, 2011

(65) Prior Publication Data

US 2012/0116435 A1    May 10, 2012

Related U.S. Application Data

(60) Provisional application No. 61/333,757, filed on May 12, 2010.

(51) Int. Cl.
*A61B 17/00* (2006.01)

(52) U.S. Cl.
USPC ............................................. 606/205; 606/1

(58) Field of Classification Search
USPC ............ 606/1, 174, 175, 205, 206, 207, 208, 606/210
See application file for complete search history.

(56) References Cited

U.S. PATENT DOCUMENTS

| | | | | |
|---|---|---|---|---|
| 1,274,669 A | * | 8/1918 | Bohn, F. ....................... | 606/206 |
| 1,988,218 A | * | 1/1935 | Segal ............................. | 606/210 |
| 5,222,973 A | * | 6/1993 | Sharpe et al. .................. | 606/206 |
| 5,242,458 A | * | 9/1993 | Bendel et al. .................. | 606/147 |
| 5,318,589 A | * | 6/1994 | Lichtman ...................... | 606/205 |
| 5,498,256 A | * | 3/1996 | Furnish ............................. | 606/1 |
| 5,499,997 A | * | 3/1996 | Sharpe et al. .................. | 606/206 |
| 5,501,698 A | * | 3/1996 | Roth et al. ..................... | 606/205 |
| 5,618,306 A | * | 4/1997 | Roth et al. ..................... | 606/205 |
| 5,618,307 A | * | 4/1997 | Donlon et al. ................. | 606/205 |
| 5,638,827 A | * | 6/1997 | Palmer et al. ................. | 600/564 |
| 5,645,075 A | * | 7/1997 | Palmer et al. ................. | 600/562 |
| 5,700,275 A | * | 12/1997 | Bell et al. ...................... | 606/208 |
| 5,810,877 A | * | 9/1998 | Roth et al. ..................... | 606/205 |
| 5,928,263 A | * | 7/1999 | Hoogeboom ................. | 606/205 |
| 6,019,758 A | * | 2/2000 | Slater ............................. | 606/51 |
| 6,024,748 A | * | 2/2000 | Manzo et al. ................. | 606/153 |
| 6,123,678 A | * | 9/2000 | Palmer et al. ................. | 600/567 |
| 6,364,891 B1 | * | 4/2002 | Doble ............................ | 606/184 |
| 6,443,968 B1 | * | 9/2002 | Holthaus et al. ............. | 606/169 |
| 2001/0056286 A1 | * | 12/2001 | Etter et al. ..................... | 606/205 |
| 2008/0188877 A1 | * | 8/2008 | Hickingbotham ............. | 606/162 |

* cited by examiner

*Primary Examiner* — Ryan Severson
*Assistant Examiner* — Jonathan W Miles
(74) *Attorney, Agent, or Firm* — Jerry A. Schulman

(57) ABSTRACT

A surgical tool has a handle from which a carriage is extendable and retractable responsive to the movement of handle leaf segments. Squeezing the leaf segments together extends the carriage from one end of the handle. A guide tube is attached to the carriage and a pair of opposed spring steel segments are positioned within the guide tube. One end of each spring steel segment is attached to the interior of the handle. The spring steel segments are biased to normally move away from each other when unrestrained. As the tube is extended from the handle it contacts the spring steel segments and forces them toward each other, thereby operating a tool formed at the tips of the spring steel segments. Different operating feels are imparted to the handle by varying the size and number of the leaf segments.

14 Claims, 4 Drawing Sheets

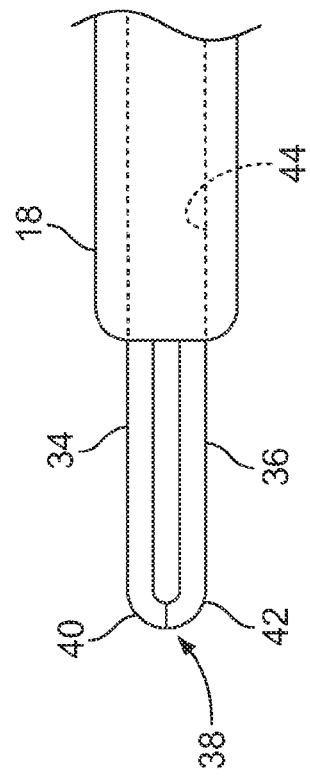
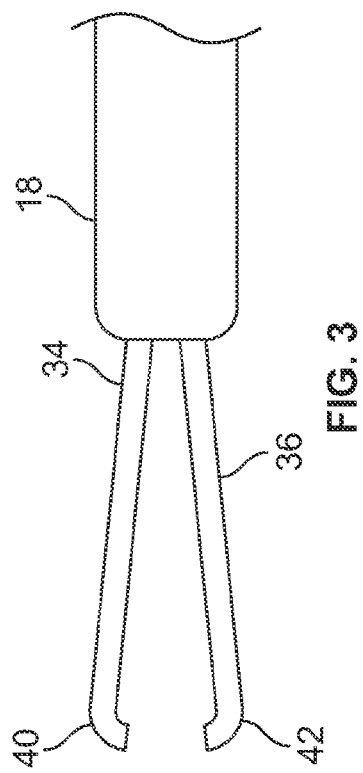
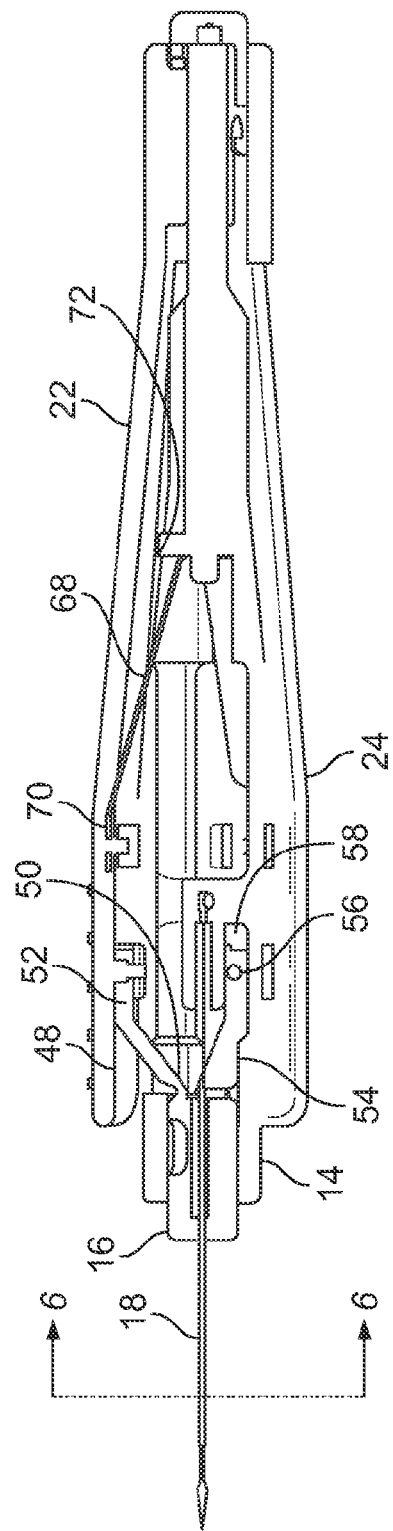

HANDLE FOR SURGICAL FORCEPS AND THE LIKE

This application claims priority from U.S. Provisional Patent Application Ser. No. 61/333,757 filed May 12, 2010, which is incorporated herein in its entirety by reference.

BACKGROUND OF THE INVENTION

The present invention relates generally to surgical instruments and, more particularly, to a handle mechanism for surgical instruments used in ophthalmic surgery such as forceps, scissors and other instruments having a surgical device that includes tips which move in response to the movement of the handle mechanism.

In one such instrument the surgical device is a pair of spring steel segments inserted into a guide tube attached to a handle. Each spring steel segment has a constant cross sectional dimension and is identical in dimension to the mating spring steel segment. For the purposes of this description, the spring steel segment assembly will be referred to as having a left hand and a right hand segment which are mirror images of each other. Each segment has an inner and an outer surface and, when assembled, the inner surfaces abut one another. The steel segments are manufactured to have a spring bias such that when the segments are unrestrained they curve away from each other.

At the distal end of each spring steel segment a tip is formed, shaped as a tool to carry out an action useful in surgery, such as gripping or cutting.

The handle includes a carriage to which the guide tube is attached. The carriage is movable axially within the handle responsive to the actuation of a leaf-type handle mechanism. As the tube is extended from the handle the tube contacts the biased-apart spring steel segments and the tips are forced towards one another. Such instruments are capable of performing different surgical tasks depending upon the design of the tool formed at the tips. For example, the tips can be formed as a pair of jaws useful as a forceps, with the jaws alternately grasping and releasing tissue as the handle mechanism is operated. The tips can also be formed as a pair of scissor blades which, when reciprocated by the handle mechanism can be used to cut tissue. The motion of the tips will continue so long as the handle mechanism is operated.

BRIEF DESCRIPTION OF THE INVENTION

A handle for an ophthalmic surgical instrument has an actuating mechanism operable by squeezing one or more handle segments, or "leaves" to move a carriage inwardly or outwardly within the handle body to cause the extension or retraction of a guide tube within which a surgical device is positioned. Preferably, the surgical instrument is of the type that is actuated when the tube is extended from or retracted into the handle body.

Preferably the handle leaves are formed integrally with the handle body and, in their unstressed or "at rest" position extend away from the handle body. A linkage extends from each handle leaf to the carriage assembly and is constructed such that when the handle leaves are squeezed or moved toward the handle body, the carriage is moved accordingly. As the leaves are released they will return to their unstressed position.

In the embodiment presented, the surgical device includes a pair of facing flexible segments biased to be spaced apart one from the other when unrestrained. When the guide tube is moved to contact the surgical device the segments are forced together, thereby operating the tool formed at the segment tips. It should be understood that, if desired, the guide tube can be anchored and the surgical device moved to bring the ramps into contact with the guide tube.

A preferred embodiment of the present invention uses three leaves that perform the actuating function. The leaves may be identical in size or may vary in size with some leaves being larger than others. Various combinations of leaf sizes produce a characteristic feel for the instrument giving the surgeon a choice of instruments from which to choose one that will be comfortable to the surgeon's style and preferences.

Preferably, the handle is constructed principally of recyclable plastic with a minimum of moving parts so that the resulting handle is light in weight and is particularly suited for single-use applications, whereby the instrument is discarded after use.

Biasing springs may be used to hold the leaves in their outward or unstressed position and to provide a characteristic "feel" to the handle mechanism, by opposing the inward motion of the leaves and by adding a return force when the leaves are allowed to move toward their unstressed position. The instrument can be adapted for use as a forceps, a scissors or other ophthalmic surgical instrument by selecting the configuration of the instrument inserted within the guide tube.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further aspects of the present invention will best be appreciated by referring to the accompanying drawings in which:

FIG. 3 is a first enlarged view of the surgical device tip;

FIG. 4 is a second enlarged view of the surgical device tip;

FIG. 5 is a lateral view with portions of the insert removed to reveal the inner configuration;

DETAILED DESCRIPTION OF THE DRAWINGS

Figure 1:
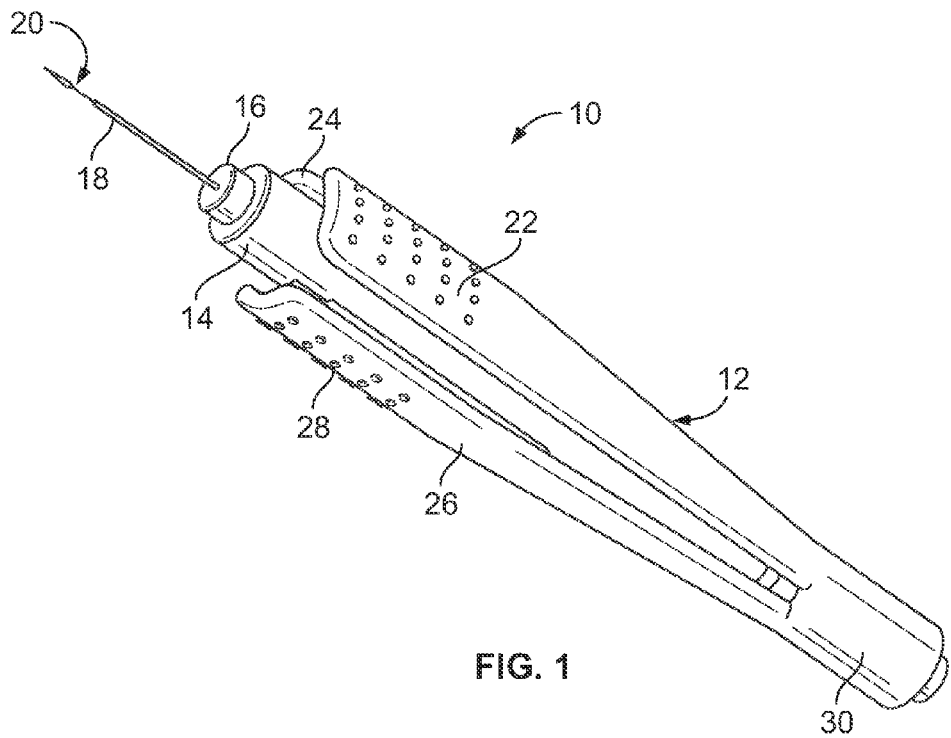
FIG. 1 is a perspective view of a surgical instrument embodying certain aspects of the present invention.

Referring now to FIG. 1, the numeral 10 identifies generally a surgical instrument having a handle assembly 12, an instrument body 14, a tube mount 16, a guide tube 18 and a surgical device 20. In the embodiment shown, handle assembly 12 comprises three handle segments or "leaves" 22, 24 and 26. Each leaf has a grip portion 28 shown by way of example on leaf 26 which, in the embodiment shown, comprises an array of raised hemispherical dots to provide a secure grip.

As seen in FIG. 1, leaves 22, 24, and 26 are integrally formed with proximal end 30 of handle 10 and are able to flex when squeezed together.

Figure 2:
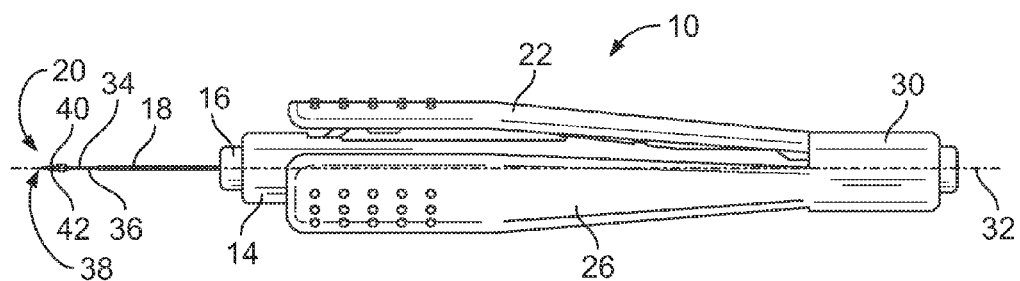
FIG. 2 is a lateral view of the instrument of FIG. 1.

Referring now to FIG. 2, a lateral view of instrument 10 is shown. In this view, leaves, 22, 26 are visible. Preferably, leaves 22, 24 and 26 are formed such that in their normal unstressed position they extend away from axis 32 of handle 10. In the embodiment shown, mount 16 is retracted into handle body 14 and leaves 22, 24 and 26 are in their unstressed position. As seen, handle body 14 has a distal end 44 sized and shaped to slidably receive cylindrical mount 16. As further seen, guide tube 18 is embedded within mounting block 16 such that when mounting block 16 is moved along axis 32, guide tube 18 moves axially as well.

Surgical device 20 will commonly comprise upper and lower surgical steel segments 34, 36 terminating at a tip 38. In the embodiment shown, tip 38 comprises upper and lower tip segments 40, 42, and segments 34, 36 are formed with permanently-curved sections that are spaced apart one from another when no force is applied to the segments, and which are constructed such that segments 34, 36 are moved either toward each other or away from each other responsive to the movement of segments 34, 36 within guide tube 18. When segments 34, 36 are unstressed, tip segments 40, 42 are spaced apart in an "open" position Referring now to FIG. 3, an enlarged view of surgical device 20 is shown. In this embodiment, surgical device 20 has been constructed as a forceps meaning that tips 40, 42 are shaped to grip selected tissue or objects during surgery and, as shown in FIG. 3, are normally held in a space-apart position when mount 16 and guide tube 18 are in their retracted position.

As seen in FIG. 4, when guide block 16 is extended from handle body 14, it moves guide tube 18 forward to bring guide tube inner wall 44 into contact with segments 34, 36 thereby forcing tip segments 40, 42 together to form closed tip Referring now to FIG. 5, instrument 10 is shown in a partially disassembled view.

Figure 7:
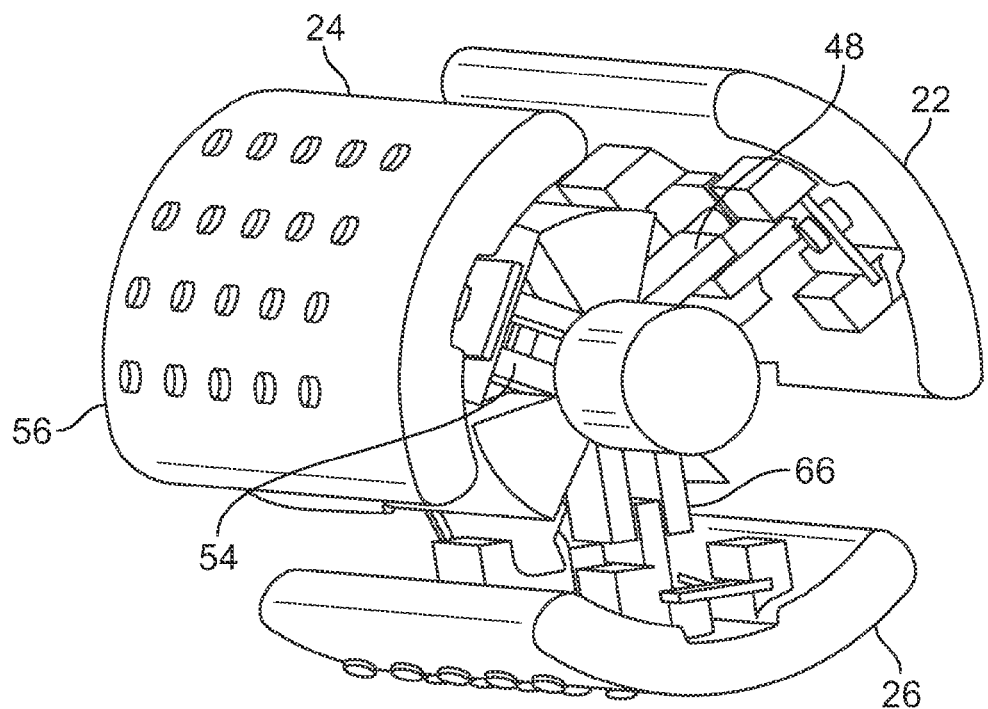
FIG. 7 is a partial perspective view of the actuating mechanism.

Mounting block 16 has integrally formed therewith a number of block linkages. There is preferably one linkage for each leaf formed on the handle. In FIG. 5, leaf 22 has block linkage 48 attached thereto. Preferably, linkage 48 is joined to mount 16 at a living hinge 50 and is attached to leaf 22 at a hinge 52. This allows linkage 48 to flex relative to mounting block 16 without requiring the use of additional parts such as pins, mounts, hinges and the like. In similar fashion, a second linkage 54 is formed on mounting block 16, and is attached to leaf 24. As seen in this view, linkage 54 is fitted to a mounting pin 56 found on leaf 24. As seen in FIG. 7, leaf 26 has a third linkage 66 attached at one end to mounting block 16 at a living hinge and at the other end to an attachment site formed on leaf 26.

Not specifically shown in FIG. 5 are the attachment sites for surgical device segments 34, 36. Preferably, segment 34, 36 are attached to an interior mount in handle 10 such that they are fixed in position and do not extend or retract.

As seen in FIG. 5, leaf 24 has a leaf channel 58 formed therein within which linkage 54 is seated and attached.

Figure 6:
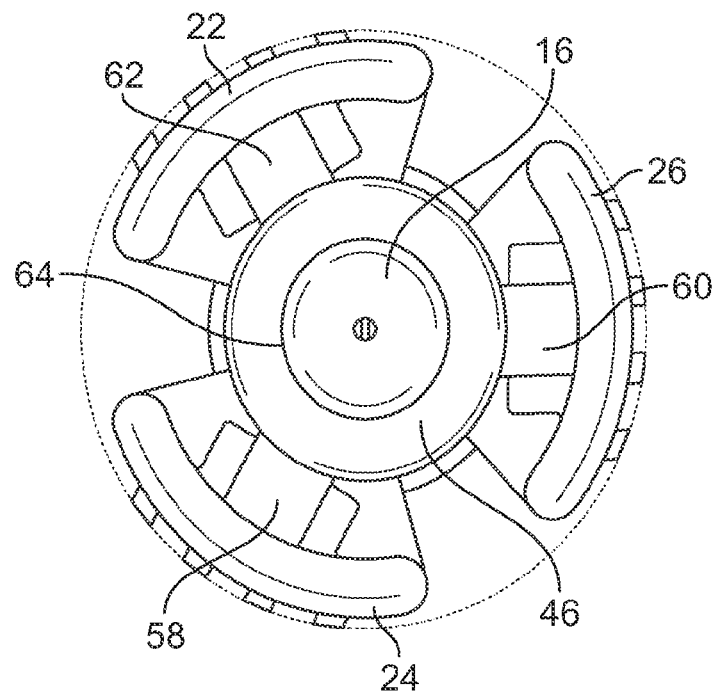
FIG. 6 is a view along 4-4 of FIG. 3.

Referring now to FIG. 6, a view is shown along 6-6 of FIG. 5 with linkages 48, 54 and 66 removed for clarity. As seen in FIG. 6, slot 58 of leaf 24 is shown as are slots 60 on leaf 26 and 62 on leaf 22. Also shown are distal end 46 and mounting block 16 as well as mount cavity 64 within guide tube 18 is seated and attached.

Referring again to FIG. 5, a return spring 68 is shown anchored at one end to leaf 22 at anchor 70 and anchored at its other end to handle body 14 at anchor 72. It should be understood that similar springs are attached to the remaining leaves 24 and 26 as well. Spring 68 is preferably a metallic leaf-type spring and is selected to give the action of leaves 22, 24 and 26 a characteristic feel when said leaves are squeezed or released, allowing the surgeon to more accurately control the operation of the surgical device.

Figure 8:
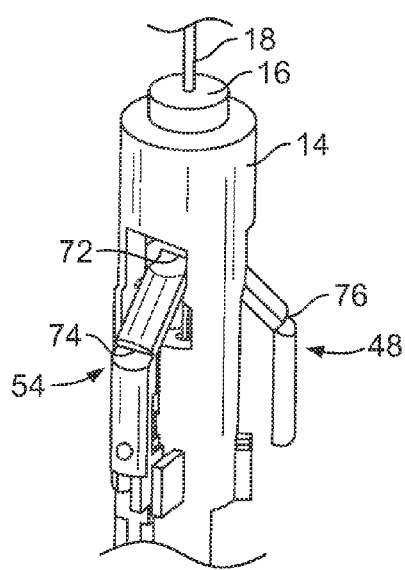
FIG. 8 is a partial perspective view of the actuating mechanism.

Referring now to FIG. 8, a detail in perspective of linkages 48 and 54 is shown. As seen, linkage 54 is joined to mounting block 16 at a living hinge 72. In this embodiment, an intermediate living hinge 74 is formed on linkage 54 to add to the flexibility and mobility of linkage 54. In similar fashion, an intermediate living hinge 76 is formed on linkage 48. It is to be understood that a similar intermediate living hinge is also formed on linkage 52.

Figure 9:
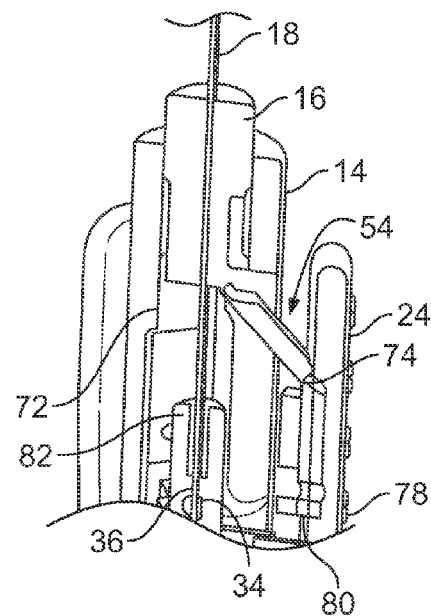
FIG. 9 is a partial sectional view of the mechanism of FIG. 8.

Referring now to FIG. 9, linkage 54 is shown in detail joined to mounting block 16 at living hinge 72 and joined to leaf 24 at hinge 78 by pin 80. Intermediate living hinge 74 is also shown. The arrangement shown in FIG. 9 demonstrates leaf 24 in its unstressed position. When leaf 24 is pushed toward body 14, mounting block 16 is urged forward as is tube 18.

Also seen in FIG. 9, surgical device segments 34, 36 are held within handle 12 by mount 82.

Figure 10:
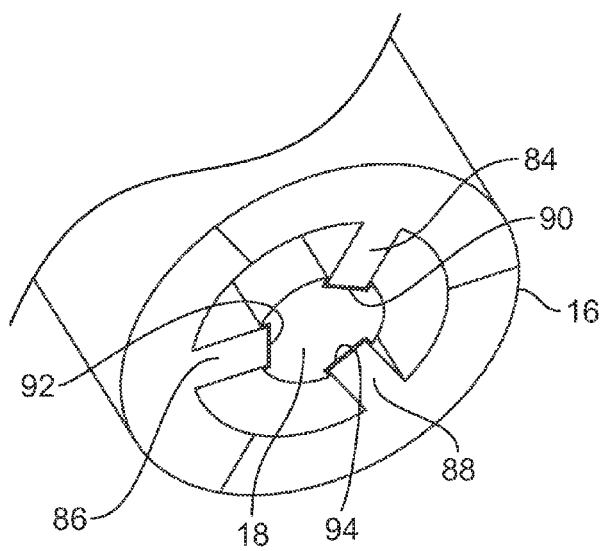
FIG. 10 is a partial perspective view of a tip and tube.

Referring now to FIG. 10, a detail of mounting block 16 is shown. In this embodiment, mounting block 16 has guide ribs 84, 86 and 88 extending radially inwardly. Guide tube 18 has channels 90, 92 and 94 formed longitudinally therealong to mate with guide ribs 84, 86 and 88 respectively. In this fashion, guide tube 18 is prevented from twisting when instrument 10 is used.

Figure 11:
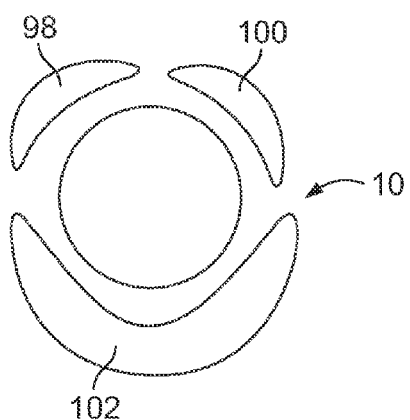
FIG. 11 is a plan view showing various sizes of handle leaves combined in a single instrument.

Referring now to FIG. 11, a partial schematic view of instrument 10 is shown with instrument body surrounded by leaves 98, 100 and 102. As seen, leaf 98 and 100 are of approximately equal size and each is smaller than leaf 102. This configuration will present a different feel to the instrument when leaves 98, 100 and 102 are actuated.

It should be understood that combinations of various sizes of leaves may be used to provide varying degrees of maneuverability, manipulability and comfort for the surgeon.

What is claimed is:

1. A surgical instrument comprising:
a handle having a proximal end and a distal end,
at least a portion of said handle having a handle cavity
said cavity terminating at a mouth at said distal end;
a carriage,
said carriage slidably received by said handle cavity at said mouth,
a guide tube,
said guide tube attached to and extending axially from said carriage whereby said tube extends outside said handle;
first and second flexible segments,
said segments positioned in a substantially parallel, axially extending relationship,
each said segment positioned within and extending from said guide tube,
each said segment having a first end and a second end,
each said first end attached to said handle,
each said second end having a tool portion formed thereat,
at least a portion of each said first and second steel segments biased to be spaced apart one from the other;

means for moving said carriage axially to extend from and retract into said mouth, said moving means comprising at least one handle leaf segment, each said handle leaf segment having a proximal end and a distal end, each said leaf segment proximal end attached to said handle at a site proximate said handle proximal end, whereby each said leaf segment may be flexed at said attachment site with respect to said handle;

at least one carriage link, each said carriage link having a first and second end, each said link having a living hinge formed intermediate said first and second ends, each said leaf segment having a first carriage link end attached to said leaf segment proximate said leaf segment distal end, each said carriage link second end attached to said carriage, whereby said carriage and, thereby said tube, is moved axially responsive to the flexing of said leaf segments and, whereby, said tube contacts said flexible segments to force said segments together to operate said tool portion.

2. The apparatus as recited in claim 1 wherein said moving means comprises three said handle leaf segments.

3. The apparatus as recited in claim 1 wherein each said carriage link is pivotally attached to one said handle leaf segment.

4. The apparatus as recited in claim 1 wherein each said carriage link is pivotally attached to said carriage.

5. The apparatus as recited in claim 1 wherein said tool portion comprises a jaw.

6. The apparatus as recited in claim 1 wherein said carriage has a central mounting bore within which said guide tube is mounted.

7. The apparatus as recited in claim 6 wherein said guide tube has a first mating surface formed thereon;

said bore has a second mating surface formed therein, said first and second mating surfaces sized and positioned to engage one another when said tube is inserted into said carriage.

8. The apparatus as recited in claim 1 wherein each said leaf segment has a first, unstressed position in which it is held apart from said handle.

9. The apparatus as recited in claim 8 wherein said leaf segment and said attachment site form a living hinge, said hinge biasing said leaf segment to said first, unstressed position.

10. The apparatus as recited in claim 8 wherein said handle further comprises a spring having two ends, said first spring end attached to said handle, and said second spring end attached to one said handle leaf segment, whereby said handle leaf segment is biased to said first, unstressed position.

11. The apparatus as recited in claim 1 wherein said tool portion comprises a scissors.

12. The apparatus as recited in claim 1 wherein said instrument comprises at least two said handle leaf segments, at least one said handle leaf segment being different in size than the other handle leaf segment or segments.

13. The apparatus as recited in claim 12 wherein said instrument comprises three said segments, two of said segments being smaller in size than the remaining segment.

14. The apparatus as recited in claim 12 wherein said instrument comprises three said segments, two of said segments being larger in size than the remaining segment.

* * * * *